United States Patent [19]

Thomas

[11] 4,089,944

[45] May 16, 1978

[54] RAPIDLY SOLUBILIZED AHF COMPOSITION AND PROCESS FOR PREPARING SAME

[75] Inventor: William R. Thomas, Laguna Niguel, Calif.

[73] Assignee: Baxter Travenol Laboratories, Inc., Deerfield, Ill.

[21] Appl. No.: 729,758

[22] Filed: Oct. 5, 1976

Related U.S. Application Data

[63] Continuation-in-part of Ser. No. 643,178, Dec. 22, 1975, abandoned.

[51] Int. Cl.$^2$ .................... A61K 35/14; A61K 47/00
[52] U.S. Cl. .................................. 424/101; 424/176; 424/361
[58] Field of Search .................. 424/101, 176, 361

[56] References Cited

U.S. PATENT DOCUMENTS

| | | | |
|---|---|---|---|
| 2,826,533 | 3/1958 | Fowell | 424/101 |
| 3,057,781 | 10/1962 | Mace et al. | 424/101 |
| 3,973,002 | 8/1976 | Hagan et al. | 424/101 |

FOREIGN PATENT DOCUMENTS

| | | |
|---|---|---|
| 1,372,515 | 10/1974 | United Kingdom. |

*Primary Examiner*—Donald B. Moyer
*Attorney, Agent, or Firm*—Paul C. Flattery; Lawrence W. Flynn; Max D. Hensley

[57] ABSTRACT

The rate of solubility of a freeze-dried solid composition containing therapeutic amounts of anti-hemophilic factor (AHF) is greatly increased by carrying out the solubilization in the presence of at least a critical threshold amount of a water soluble carbohydrate. The carbohydrate is incorporated into the AHF composition in sufficient quantity to provide at least 2 weight units of carbohydrate (expressed in grams) per 100 volume units of AHF solution (expressed in milliliters). This enhanced rate of solubility permits rapid treatment of hemophilic patients.

36 Claims, 1 Drawing Figure

Grams Dextrose/100 ml. of Reconstituted Solution

RAPIDLY SOLUBILIZED AHF COMPOSITION AND PROCESS FOR PREPARING SAME

CROSS REFERENCE TO RELATED APPLICATIONS

This is a continuation-in-part of application Ser. No. 643,178, filed Dec. 22, 1975 now abandoned.

BACKGROUND OF THE INVENTION

As is known in the art, blood plasma (blood from which white and red blood cells and blood platelets have been removed) is a fluid containing about 90 percent water and 10 percent solids. Reduced amounts of blood plasma are used today since processes have been developed whereby the water from the plasma is removed and the solids then divided into a number of therapeutically useful fractions. Patients receive only the fraction they need and not the entire plasma. Among these plasma fractions which are clinically used are the fibrinogen fraction and the anti-hemophilic factor (AHF, Factor VIII) fraction. The latter fraction normally contains some fibrinogen as well.

Both of these fractions are generally freeze-dried to remove the water and, just prior to use, are dissolved in a liquid aqueous media to form a solution which is then injected into the patient. Time is of considerable importance to the person (e.g. the doctor or nurse) administering the fibrinogen fraction or the AHF fraction, because loss of blood by the hemophiliac and/or injury to the joints is aggravated during the time required for preparation of the solution. Thus it is desirable that the solid product dissolve in the aqueous media in a relatively short period of time.

It is known that the time of solubilization of the fibrinogen fraction can be reduced by adding dextrose thereto. Dextrose has also been added to AHF. For example, the "Journal of Thrombosis Research", Volume 1, pages 191–200, 1972, published by Pergamon Press, Inc. reported that dextrose was added to AHF in order to facilitate the chromatography of AHF. The article concluded that the yield of bovine Factor VIII from chromatography on anion exchange media can be greatly improved by the inclusion of a low-molecular weight carbohydrate, such as dextrose, in the solvents. In addition to the foregoing, the inventor is also aware that Cutter Laboratories, Inc. has added sufficient dextrose to its commercial AHF preparation so that when the preparation is reconstituted according to the instructions, the resulting AHF solution contains about one gram of dextrose per 100 milliliters of solution.

U.S. Pat. No. 2,826,533 discloses the addition of dextrose to the fibrinogen fraction. U.S. Pat. No. 3,057,781 discloses stabilizing plasma with invert sugar and levulinic acid; the carbohydrates herein, however are free of levulinic acid.

SUMMARY OF THE INVENTION

A primary object of the present invention is to provide a clinically useful freeze dried solid composition containing AHF and fibrinogen which is rapidly soluble in an aqueous medium at room temperature, said solubility being due to the presence of a critical threshold amount of a water soluble carbohydrate in the system during solubilization.

A further object of the present invention is to provide a method for producing a freeze-dried solid composition containing AHF and fibrinogen by fractionating blood plasma with polyethylene glycol to obtain a precipitate comprising AHF and fibrinogen, dissolving the precipitate in aqueous media and freeze-drying the resulting solution to obtain essentially a dry solid composition useful for clinical purposes, said freeze-dried composition being readily soluble in an aqueous medium at room temperature.

Other and further objects of the present invention will be apparent from the following detailed description.

DESCRIPTION OF THE PREFERRED EMBODIMENTS

Figure 1:
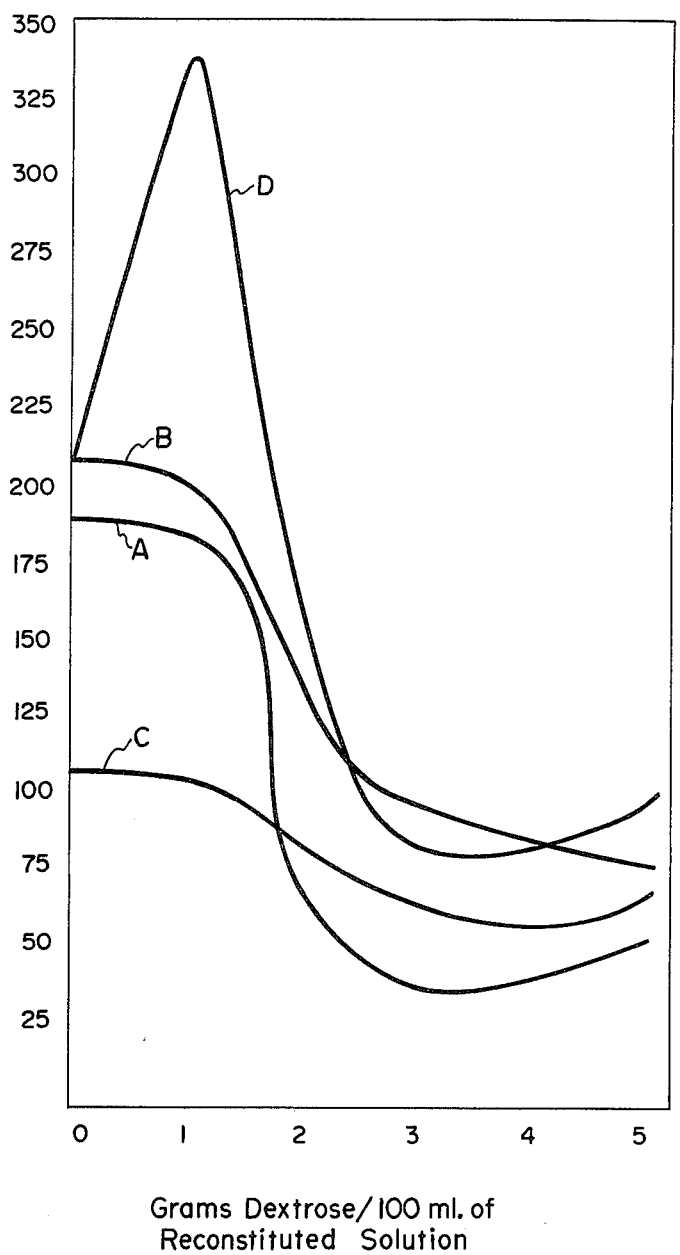
FIG. 1 graphically depicts the unexpected dramatic improvement in the rate of solubilization of solid compositions containing AHF which is obtained when the composition is solubilized in the presence of from 0 to 5 grams of dextrose per 100 ml. of reconstituted solution. The various curves are obtained using different reconstitution temperatures and volumes.

The foregoing objects, and others, are accomplished by the present invention by the inclusion of a water soluble carbohydrate in the solid material comprising AHF. When one desires to use the composition, one need only add the requisite amount of water to obtain the desired concentration of AHF. Because of the presence of the carbohydrate, the composition dissolves in a very short period of time, for example, less than 1 minute, and can then be injected into the patient.

The amount of carbohydrate to be added is critical in the sense that mere addition of carbohydrate does not in itself result in significant solubilization time improvements. A threshold concentration of carbohydrate must be reached before useful improvements in solubilization time are achieved, after which addition of more carbohydrate again exerts no significant effect on solubilization time. This threshold concentration will vary within the ranges infra depending upon factors which are believed to include the amount and identity of protein and salts in the AHF preparations as well as the identity of the carbohydrate selected. The exact optimum quantity of carbohydrate will thus vary with the carbohydrate chosen, the method of AHF preparation and even with separate runs using the same preparatory method. Thus the appropriate quantity should be determined by elementary and conventional solubilization time assays for each lot of AHF.

The amount of carbohydrate should be sufficient to bring the solid AHF preparation into solution within about 90 seconds, and preferably 65 seconds, the AHF being present in the solid composition in an amount sufficient to form a therapeutically effective AHF concentration upon solubilization of the composition. A therapeutically effective concentration of AHF in such solutions illustratively ranges about from 3 to 100 International Units of AHF per ml. with a preferred range of about from 3 to 40 International Units per ml. The amount of carbohydrate present in the solid AHF composition typically provides, upon reconstitution with water, an aqueous solution or other suitable reconstituting liquid, a therapeutically effective solution of AHF containing at least about 2 weight units of carbohydrate (computed in grams) for every 100 volume units of solution (computed as milliliters). The amount of carbohydrate will generally vary about from 2 to 10 grams, preferably about 2 to 5 grams of carbohydrate per 100 ml. of solution, with about 3 grams appearing to be optimum.

To provide the desired concentration of carbohydrate in solution, the carbohydrate is illustratively present in the solid composition in an amount of about 1.6 to 7.5 times the amount of total protein in the solid AHF composition. Preferably, the amount of carbohydrate is about 2.0 to 5.0 times the weight of total protein. The preferred embodiment is about 2.0 times the weight of total protein. This solid composition can contain anywhere from about 2 to 200 International Units of AHF/gm. protein, and still produce as a practical matter a solution of AHF upon reconstitution which has a therapeutically significant effect.

The water soluble carbohydrates useful in the invention include any which are capable of hydrating the AHF-containing composition. This includes without limitation the monosaccharides such as the commonly available hexoses, including dextrose (glucose), mannose, galactose and fructose; the disaccharides such as maltose, lactose and sucrose; the trisaccharides, such as raffinose; and the short chain dextrins, e.g. dextrins having a chain length of less than about four monosaccharide units. Mixtures of suitable carbohydrates may also be employed. The preferred carbohydrates are dextrose, sucrose, maltose and lactose, with dextrose being an especially preferred material. The carbohydrate must be biologically acceptable and otherwise comply with appropriate Federal regulations when the AHF is commercially marketed for human administration. The carbohydrate can be admixed with the AHF-containing composition at any point during or prior to preparation of the lyophilized composition.

There are of course numerous procedures known to those skilled in the art to prepare AHF compositions whose rate of solubility is enhanced by the addition of carbohydrate in accordance with the present invention. In the preferred embodiment, the solid mixture comprising AHF and fibrinogen is obtained by starting with plasma frozen at about minus 25° C. which is then thawed to 4° to 5° C. to produce a cryoprecipitate which is collected by centrifugation.

The cryoprecipitate is suspended in heparinized, citrated saline to which is added 3.5% by weight, of polyethylene glycol. The resulting mixture is centrifuged and the resulting fibrinogen precipitate is discarded and the supernatant retained. To the supernatant is added about 7.5 weight units of polyethylene glycol (expressed as grams) per 100 volume units of supernatant (expressed as milliliters). The resulting suspension is mixed for about 15 minutes at room temperature and is then centrifuged and the resulting precipitate collected. This precipitate or solid mixture comprises AHF and fibrinogen and can be used as such or can be further purified by glycine fractionation. In any event, the water soluble carbohydrate can be added to either of such mixtures. Preferably, the solid mixture is dissolved in an aqueous medium, for example, a dextrose citrated saline aqueous solution containing about 0.72% sodium chloride, 0.02M sodium citrate and an appropriate amount of dextrose to produce the desired effect of an enhanced rate of solubilization. It is neither necessary nor desirable at this stage to add water to the point where the solution contains about 2 weight units of dextrose per 100 volume units of solution since such a dilute solution may unnecessarily extend the time required for lyophilization.

The dissolved solid mixture containing the dextrose is further clarified by passing it through a coarse filter which removes some of the fibrinogen and other insoluble proteins. Thereafter, the sample is further diluted with citrated saline, as desired, to a potency of about 3 to 75 International Units/ml. or left as a concentrate which normally contains from 250 to 1000 International Units/ml. The dissolved product is then sterile filtered through a "Millipore" membrane filter having an average pore size of about 0.3 microns. The filtered solution is filled under aseptic conditions into 10 ml. to 30 ml. capacity vials, as desired, rapidly frozen and freeze-dried.

To administer the AHF preparation to a patient, the normal procedure is to reconstitute the lyophilized material to a solution containing about 3 to about 100 International Units of AHF per ml., and more commonly about 24 to about 28 Units per ml., about 2 to about 10 grams of dextrose per 100 ml., about 1.4 to about 1.6 grams of protein per 100 ml., about 0.6 to about 0.8 grams of fibrinogen per 100 ml., and about 0.7 gram to about 6 grams of salts such as NaCl, sodium citrate, glycine and unidentified residual solids per 100 ml. Typically a 10 ml. vial of reconstituted AHF solution will contain about 270 International Units of AHF, about 0.3 gram of dextrose, about 0.15 gram of protein including about 0.07 gram of fibrinogen, about 0.51 gram of residuals and sufficient water to 10 ml. volume.

The lyophilized product is readily soluble in sterile water at room temperature and after the addition of the water is almost immediately ready for administration to hemophilic patients as a result of the dextrose levels in the solution.

In order to show the dramatic unexpected results obtained by the present invention the following tests were conducted wherein various concentrations of dextrose were added to lyophilized AHF product obtained as above. 10 ml. and 30 ml. capacity vials containing the product were filled with 10 ml. and 30 ml., respectively, of water at room temperature and 37° C. The 30 ml. vials contained approximately three times as much product as the 10 ml. vials. The time required for complete dissolution of each sample was recorded. The results are presented below in Table 1 and in FIG. 1.

Table 1

| grams dextrose/ 100 ml. of reconstituted composition | FIG. 1 Curve: Reconstituting Volume: Diluent Temp.: | A 10 ml 37° C. | B 10 ml Room Temp. | C 30 ml 37° C. | D 30 ml Room Temp. |
|---|---|---|---|---|---|
| 1 | | 176 secs. | 195 secs. | 100 secs. | 330 secs. |
| 3 | | 35 secs. | 85 secs. | 50 secs. | 65 secs. |
| 5 | | 48 secs. | 55 secs. | 52 secs. | 75 secs. |
| None (control) | | 185 secs. | 210 secs. | 105 secs. | 210 secs. |

The control in the above table was identical to the other samples in all respects except that the control contained no dextrose.

The results of Table 1 are plotted in FIG. 1. The plotted data clearly shows the marked improvement in rate of solubility once a dextrose concentration exceeding 2 grams per 100 mls. of solution is obtained. Similar desirable results are obtained with the other carbohydrates discussed hereinabove.

In the preceding example, polyethylene glycol was used to fractionate the blood plasma. However, other compounds can be used such as ethylene oxide-propylene glycol condensation products, and other procedures for fractionation can be employed to produce a product which is rapidly soluble according to the teachings herein.

I claim:

1. A solid material comprising AHF, fibrinogen and a water soluble carbohydrate, said AHF being present in an amount sufficient to provide a therapeutically useful solution of AHF upon reconstitution in aqueous media and said carbohydrate being present in an amount sufficient to provide in said solution a carbohydrate concentration of at least about 2 grams per 100 milliliters.

2. The material of claim 1 wherein the carbohydrate is a monosaccharide.

3. The material of claim 2 wherein the carbohydrate is selected from the group consisting of dextrose, mannose, galactose and fructose.

4. The material of claim 1 wherein the carbohydrate is a disaccharide.

5. The material of claim 4 wherein the carbohydrate is selected from the group consisting of lactose, sucrose and maltose.

6. The material of claim 1 wherein the carbohydrate concentration is about 2 to about 10 grams per 100 milliliters.

7. The material of claim 1 wherein the carbohydrate concentration is about 3 grams per 100 milliliters.

8. A solid material comprising AHF and an amount of at least one water soluble carbohydrate sufficient to solubilize the material in an aqueous medium within about 90 seconds, the AHF being present in an amount sufficient to form a therapeutically effective AHF concentration upon solubilization of the material.

9. The material of claim 8 wherein the carbohydrate is dextrose.

10. A lyophilized material comprising AHF, fibrinogen and an amount of water soluble carbohydrate sufficient to solubilize the material in an aqueous solution within about 65 seconds, the AHF being present in an amount sufficient to form a therapeutically effective AHF concentration upon solubilization of the material.

11. The material of claim 10 wherein the material is dextrose.

12. A solid material comprising proteins, including AHF, and at least one water soluble carbohydrate, the amount of carbohydrate being about from 1.6 to 7.5 times the amount by weight of protein in the material.

13. The material of claim 12 wherein the amount of carbohydrate is about from 2 to 5 times the amount by weight of protein.

14. The material of claim 12 wherein the amount of carbohydrate is about 2 times the amount by weight of protein.

15. The material of claim 12 wherein the carbohydrate is dextrose.

16. The material of claim 12 wherein the AHF is present in an activity of about from 2 to 200 International Units/gm protein.

17. The material of claim 16 wherein the AHF is present in an activity of about 16 International Units/gm protein.

18. A lyophilized material comprising about 31 parts by weight of dextrose, about 16 parts by weight of protein including AHF in an activity of about 270 International Units/gm of material, and about 53 parts by weight of salts.

19. In a method for producing a clinically useful freeze-dried solid composition containing AHF and fibrinogen from blood plasma or an AHF-containing fraction thereof including the steps of fractionating the plasma to obtain a solid mixture comprising AHF and fibrinogen, dissolving the solid mixture in an aqueous medium and freeze-drying the resulting solution to obtain a clinically useful freeze-dried solid composition which is then reconstituted in a reconstitution liquid for use, the improvement comprising rendering the freeze-dried, solid composition rapidly soluble in an aqueous medium at room temperature by adding water soluble carbohydrate to the mixture, the amount of carbohydrate added being an amount sufficient to produce at least about 2 grams per 100 milliliters concentration of carbohydrate upon reconstitution of the composition in a suitable medium to produce a therapeutically useful solution of AHF.

20. The method of claim 19 wherein the carbohydrate is added to a solid mixture consisting essentially of fibrinogen and AHF.

21. The method of claim 19 wherein the carbohydrate is selected from the group consisting of dextrose, maltose, lactose and sucrose.

22. The method of claim 21 wherein the carbohydrate is dextrose.

23. The method of claim 19 wherein the amount of carbohydrate is sufficient to produce a solution having about from 2 to 5 grams of carbohydrate per 100 milliliters of solution.

24. In a method for producing a clinically useful freeze-dried solid composition containing AHF and fibrinogen from blood plasma or an AHF-containing fraction thereof including the steps of fractionating the plasma to obtain a solid mixture comprising AHF and fibrinogen, dissolving the solid mixture in an aqueous medium and freeze-drying the resulting solution to obtain a clinically useful freeze-dried solid composition which is then reconstituted in a reconstitution liquid for use, the improvement comprising rendering the freeze-dried, solid composition rapidly soluble in an aqueous medium at room temperature by adding water soluble carbohydrate to the composition, the amount of carbohydrate added being sufficient to solubilize the freeze-dried composition within about 90 seconds, the AHF being present in an amount sufficient to form a therapeutically effective AHF concentration upon solubilization of the composition.

25. The method of claim 24 wherein the amount of carbohydrate is sufficient to solubilize the composition within about 65 seconds.

26. The method of claim 24 wherein the carbohydrate is selected from the group consisting of dextrose, maltose, lactose and sucrose.

27. The method of claim 26 wherein the carbohydrate is dextrose.

28. In a method for producing a clinically useful freeze-dried solid composition which contains protein, including AHF, comprising the steps of fractionating blood plasma or an AHF-containing fraction thereof to obtain a solid mixture comprising protein, dissolving the mixture in an aqueous medium and freeze-drying the resulting solution to obtain a clinically useful freeze-dried solid composition, the improvement comprising adding water soluble carbohydrate to the composition in a proportion of about from 1.6 to 7.5 times the amount by weight of protein in the composition.

29. The method of claim 28 wherein the proportion is about from 2 to 5 times the amount by weight of protein.

30. The method of claim 28 wherein the proportion is about 2 times the amount by weight of protein.

31. The method of claim 28 wherein the carbohydrate is selected from the group consisting of lactose, dextrose, maltose and sucrose.

32. The method of claim 31 wherein the carbohydrate is dextrose.

33. A method for rapidly solubilizing a solid AHF-containing composition to produce a solution containing a therapeutically effective amount of AHF, comprising mixing said composition with an amount of carbohydrate sufficient to provide a solubilized composition containing a therapeutically effective amount of AHF and at least about 2 grams of carbohydrate per 100 milliliters of solubilized composition.

34. The method of claim 33 wherein the carbohydrate is added as an aqueous solution.

35. A method for preparing an AHF-containing composition which is rapidly solubilized upon reconstitution with a reconstituting liquid to produce a solution containing a therapeutically effective amount of AHF, which comprises adding to said composition a water soluble carbohydrate in an amount sufficient to provide upon said reconstitution a solution of AHF-containing at least about 2 grams of carbohydrate per 100 volume units of solution (expressed in milliliters).

36. The method of claim 35 wherein the method includes lyophilizing the composition and said carbohydrate is added before the composition is lyophilized.

* * * * *